(12) United States Patent
Janae et al.

(10) Patent No.: US 6,675,051 B2
(45) Date of Patent: Jan. 6, 2004

(54) SEE-THROUGH ELECTRODE-PAD PACKAGE AND METHOD FOR USING A STORAGE SYSTEM THAT INCLUDES THE PACKAGE

(75) Inventors: Christine Janae, Seattle, WA (US); Thomas Solosko, Issaquah, WA (US)

(73) Assignee: Koninklijke Philips Electronics N.V., Eindhoven (NL)

( * ) Notice: Subject to any disclaimer, the term of this patent is extended or adjusted under 35 U.S.C. 154(b) by 155 days.

(21) Appl. No.: 09/746,117

(22) Filed: Dec. 22, 2000

(65) Prior Publication Data

US 2002/0082672 A1 Jun. 27, 2002

(51) Int. Cl.[7] .................................................. A61N 1/04
(52) U.S. Cl. ........................ 607/142; 607/152; 600/372
(58) Field of Search ................................ 607/142, 149, 607/152, 153, 145, 4, 5; 600/372

(56) References Cited

U.S. PATENT DOCUMENTS

| | | | |
|---|---|---|---|
| 4,227,615 A | * | 10/1980 | Flick .......................... 200/82 R |
| 5,607,454 A | | 3/1997 | Cameron et al. |
| 5,645,571 A | | 7/1997 | Olson et al. |
| 5,735,879 A | | 4/1998 | Gliner et al. |
| 5,836,993 A | | 11/1998 | Cole |
| 5,879,374 A | | 3/1999 | Powers et al. |
| 5,951,598 A | * | 9/1999 | Bishay et al. ............... 600/372 |
| 6,115,638 A | * | 9/2000 | Groenke ..................... 600/392 |
| 6,422,669 B1 | * | 7/2002 | Salvatori et al. ............ 206/320 |

* cited by examiner

Primary Examiner—Jiping Lu

(57) ABSTRACT

An electrode-pad storage package includes an interior for storing one or more electrode pads and a window that provides a view into the interior. Because it has a window, the package often reduces the time it takes for an operator to attach the electrode pad or pads to a patient. For example, such a see-through package often saves precious seconds by allowing the operator to view the instructions on a defibrillator electrode pad or pads, and thus determine which electrode pad goes where, before opening the package. Such a package may also save time by allowing the operator to determine the pad type, and thus determine whether the electrode pad or pads are appropriate for the patient, before opening the package. In this latter case, the package may also prevent the operator from unnecessarily opening, and thus wasting, a package containing an inappropriate electrode pad or pads.

32 Claims, 8 Drawing Sheets

SEE-THROUGH ELECTRODE-PAD PACKAGE AND METHOD FOR USING A STORAGE SYSTEM THAT INCLUDES THE PACKAGE

BACKGROUND OF THE INVENTION

1. Field of the Invention

The invention relates generally to electrode pads, and more particularly to a see-through package for storing an electrode pad of a medical device such as an automatic or semi-automatic external defibrillator (AED). In one embodiment of the invention, at least a portion of the package is see-through so that one can view the electrode pad, or instructions printed on the pad, before opening the package.

2. Description of the Prior Art

AEDs have saved many lives in non-hospital settings, and, as a result of advances in AED technology, the number of lives saved per year is rising. Typically, an AED analyzes a patient's heart rhythm and instructs an operator to administer an electrical shock to the patient if appropriate. For example, a shock can often revive a patient who is experiencing ventricular fibrillation (VF). Because older models of AEDs include only basic diagnostic and safety features, they are often difficult to operate. Therefore, only specially trained persons such as emergency medical technicians (EMTs) can use these older models to administer shocks to a patient. Newer models, however, often include advanced diagnostic and safety features that allow minimally trained persons to administer shocks to patients. Consequently, more people are using AEDs to save lives.

Because a heart rhythm that responds to an electrical shock can cause permanent damage or death within a short time if left untreated, an AED operator should be able to set up and use an AED to shock a patient within seconds after the operator arrives at the scene. Statistically, for each minute that a person is in cardiac arrest and is not receiving cardiopulmonary resuscitation (CPR), his/her chance of survival decreases by 10%. And in most cases, there is no chance for resuscitation after 10 minutes. Unfortunately, many people do not know how to administer CPR. And, even in the best of circumstances, it can take a few minutes to retrieve the AED and a few additional minutes for the AED to diagnose and shock the patient. Therefore, even if the patient is discovered immediately, the operator often has little time to remove the defibrillator electrode pads from their package, attach the pads to the patient, connect the pads to the AED, and activate the AED without further decreasing the patient's chance of survival. Clearly, the faster the operator can set up and activate the AED, the better the chances that the patient will survive.

FIG. 1 is a perspective view of a conventional defibrillator-electrode-pad storage system 10, which includes a package 12 and two defibrillator electrode pads 14a and 14b (shown in phantom line) stored within an interior 16 of the package 12. Electrode-pad leads 18a and 18b, which electrically connect the electrode pads 14a and 14b to an AED (not shown in FIG. 1), extend from a sealed opening 20 in the package 12, although the leads 18a and 18b may be stored entirely within the package 12.

FIGS. 2A and 2B are front and rear views, respectively, of the electrode pad 14a of FIG. 1, it being understood that the front and rear views of the electrode pad 14b are similar.

Referring to FIG. 2A, the front of the defibrillator electrode pad 14a is typically nonconductive to insulate the AED operator (not shown in FIG. 2A) from defibrillation shocks, and typically has instructions that indicate where to attach the electrode pad 14a to the patient (not shown). For example, the front of the electrode pad 14a has an instruction picture 22a, which illustrates the proper locations 24a and 24b for attachment of the two electrode pads 14a and 14b on a patient (not shown in FIG. 2A or 2B). A dashed-line circle 26a and a bold arrow 28a indicate that the location 24a is the appropriate location for attaching the electrode pad 14a to the patient. Similarly, the front of the pad 14b (not shown in FIG. 2A) has a similar picture 22b with a dashed-line circle 26b around and an arrow 28b pointing to the location 24b, which is the appropriate location for attaching the electrode pad 14b to the patient. Indicating which electrode pad 14a and 14b is attached at which location 24a and 24b reduces operator confusion, and thus decreases the time it takes the operator to attach the electrode pads to the patient. The pictures 22a and 22b and accompanying written instructions are described in U.S. Pat. No. 5,951,598, to Bishay et al., which is incorporated by reference.

Referring to FIG. 2B, the rear of the defibrillator electrode pad 14a includes a conductive layer 30a, which is typically coated with a contact gel 32a. The gel 32a provides electrical conduction between the patient and the conductive layer 30a and helps adhere the electrode pad 14a to the patient.

Referring to FIGS. 1 and 2B, the package 12 is typically formed from an opaque material that provides a moisture barrier sufficient to maintain the viability of the defibrillator electrode pads 14a and 14b for a predetermined period or longer. Typically, the electrode pads 14a and 14b are viable only while the contact gels 32a and 32b (not shown) maintain respective moisture levels that are at or above a predetermined threshold. Therefore, the manufacturer specifies that the package 12 will limit moisture loss from the package interior 16 to a rate sufficient for maintaining adequate moisture in the gels 32a and 32b for a predetermined period such as one year. Many of the best materials for providing such a moisture barrier, and thus for composing the package 12, are opaque.

Unfortunately, referring to FIGS. 1–2B, an opaque package 12 often increases the time it takes an operator (not shown in FIGS. 1–2B) to attach the defibrillator electrode pads 14a and 14b to the patient (not shown), and thus often increases the time it takes the operator to set up the AED (not shown in FIGS. 1–2B) and shock the patient. The operator looks at the circles 26a and 26b (not shown in FIGS. 1–2B) to determine which electrode pad goes where. But because the package 12 is opaque, the operator cannot look at the circles 26a and 26b until after he/she removes the electrode pads 14a and 14b from the package. This increases the time it takes for the operator to determine which electrode pad goes where, and thus increases the time it takes for the operator to attach the electrode pads 14a and 14b to the patient. Furthermore, different electrode pads 14a and 14b are often recommended for different patients. For example, adult electrode pads 14a and 14b are recommended for adults, and pediatric electrode pads are recommended for children. Even though the pad type may be labeled on the outside of the package 12, the operator may overlook this label in his/her haste to rescue the patient and not consider the type of the electrode pads 14a and 14b until after opening the package. Therefore, if the electrode pads 14a and 14b are inappropriate for the patient, then the operator must retrieve and open at least one more set of electrode pads, thus increasing the time it takes the operator to attach the appropriate electrode pads to the patient. In addition, because electrode pads that are removed from a package should be discarded whether or not they are used, pads that are removed from package and are then found to be inappropriate for the patient typically go unused, and are thus wasted.

Consequently, there is a need for a package that maintains the viability of electrode pads such as defibrillator electrode pads and yet facilitates an operator's understanding of the pad type and of which pad goes where.

SUMMARY OF THE INVENTION

A package is provided for storing one or more electrode pads. The package includes an interior for storing the electrode pad or pads and a window that provides a view into the interior.

Because it has a window, the package often reduces the time it takes for an operator to attach one or more electrode pads to a patient. For example, such a see-through package often saves precious seconds by allowing the operator to view the instructions on a defibrillator electrode pad or pads, and thus determine which electrode pad goes where, before opening the package. Such a package may also save time by allowing the operator to determine the pad type, and thus to determine whether the electrode pad or pads are appropriate for the patient, before opening the package. In this latter case, the package may also prevent the operator from unnecessarily opening, and thus wasting, a package containing one or more electrode pads that are inappropriate for the patient.

DESCRIPTION OF THE PREFERRED EMBODIMENTS

The following discussion is presented to enable a person skilled in the art to make and use the invention. Various modifications to the preferred embodiment will be readily apparent to those skilled in the art, and the generic principles herein may be applied to other embodiments and applications without departing from the spirit and scope of the present invention as defined by the appended claims. Thus, the present invention is not intended to be limited to the embodiment shown, but is to be accorded the widest scope consistent with the principles and features disclosed herein.

Figure 1:
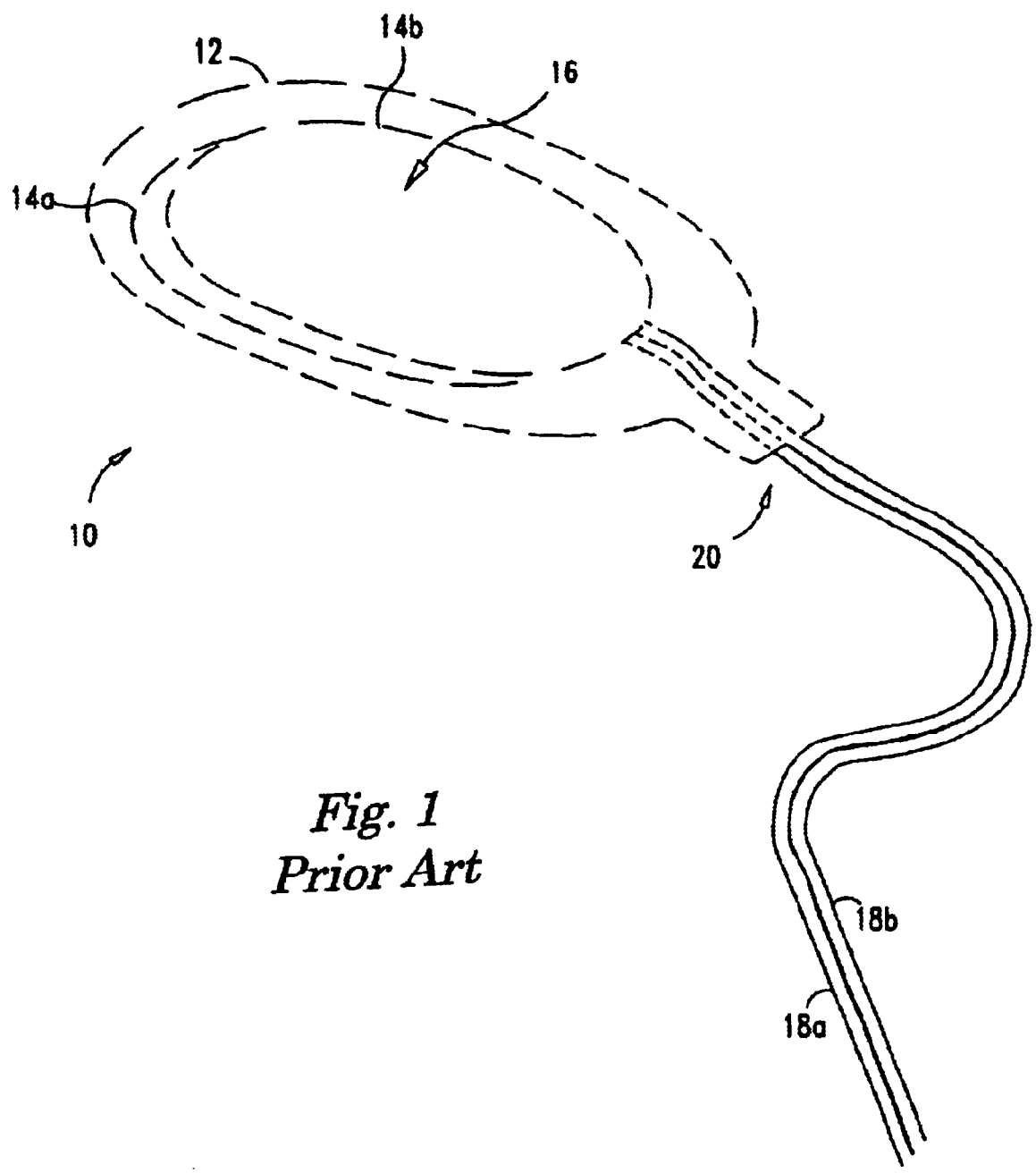
FIG. 1 is a perspective view of a conventional defibrillator-electrode-pad storage system.
Figure 2B:
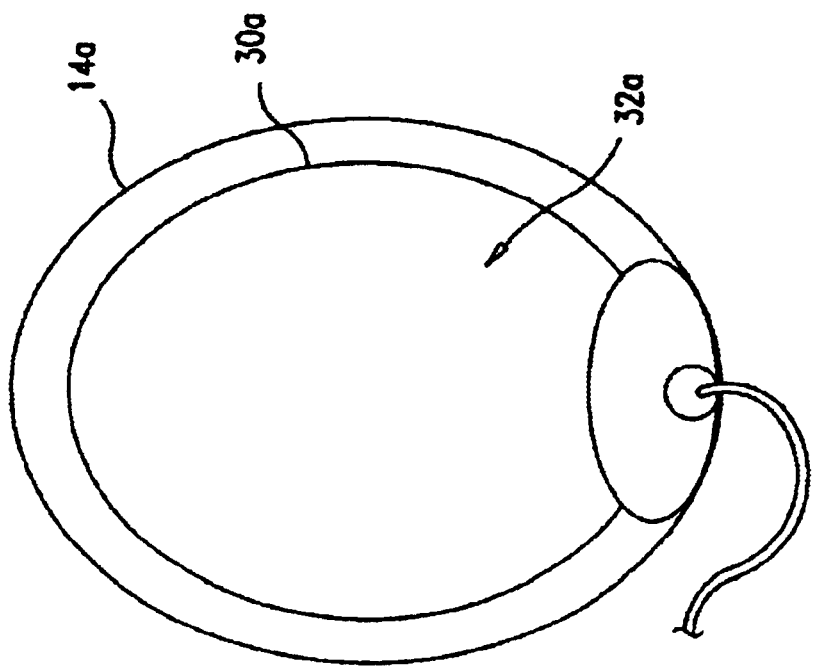
FIG. 2B is a rear view of one of the defibrillator electrode pads of FIG. 1.
Figure 2A:
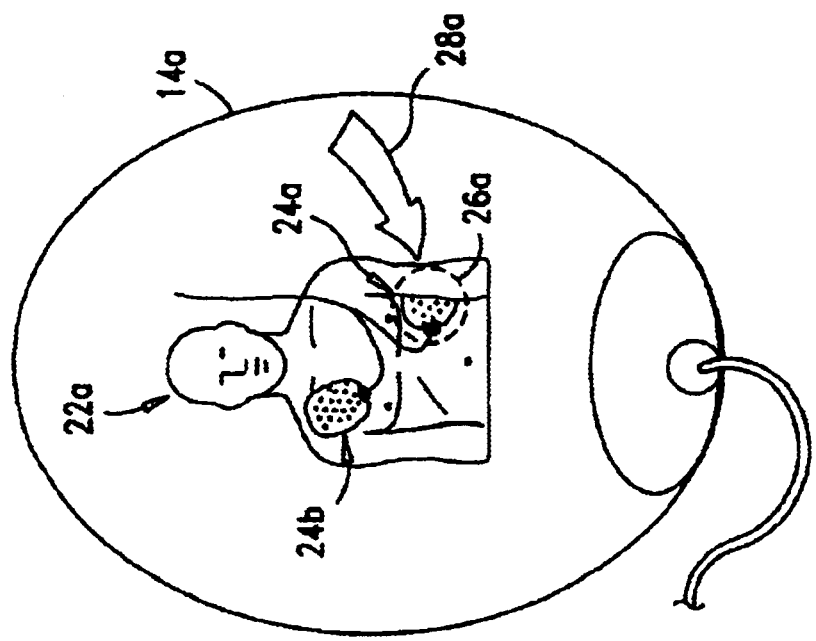
FIG. 2A is a front view of one of the defibrillator electrode pads of FIG. 1.
Figure 3B:
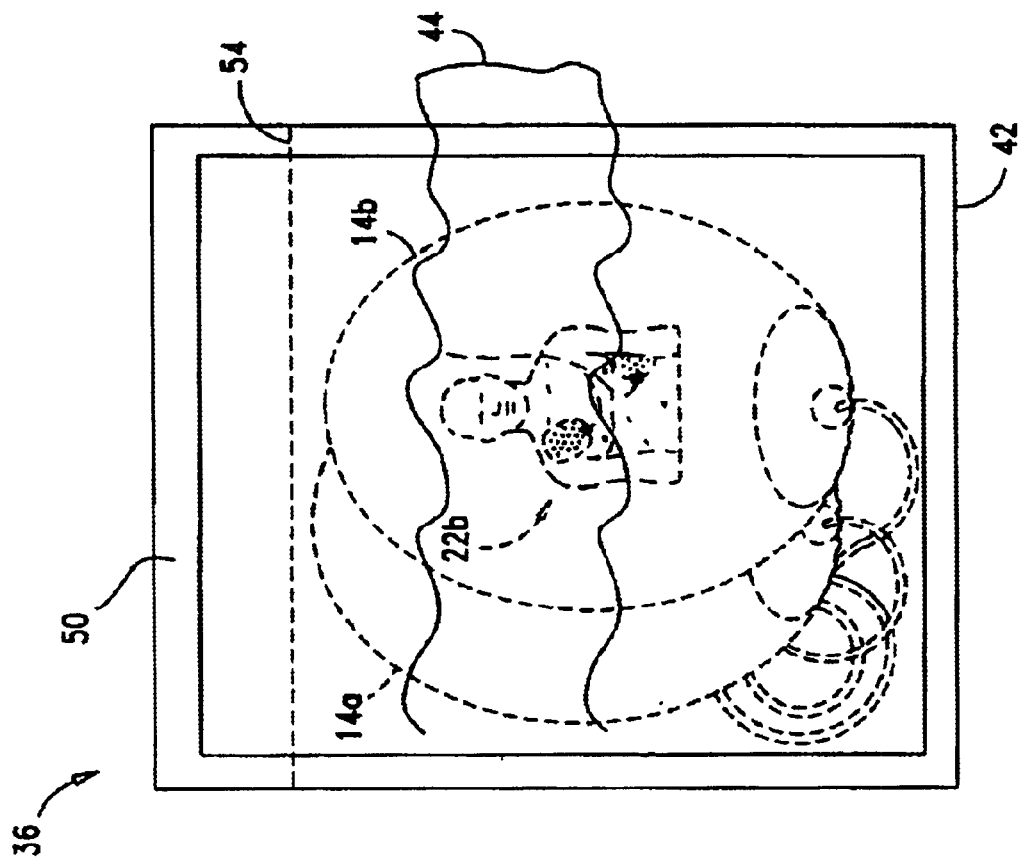
FIG. 3B is a rear view of the defibrillator-electrode-pad storage system of FIG. 3A according to an embodiment of the invention.
Figure 3A:
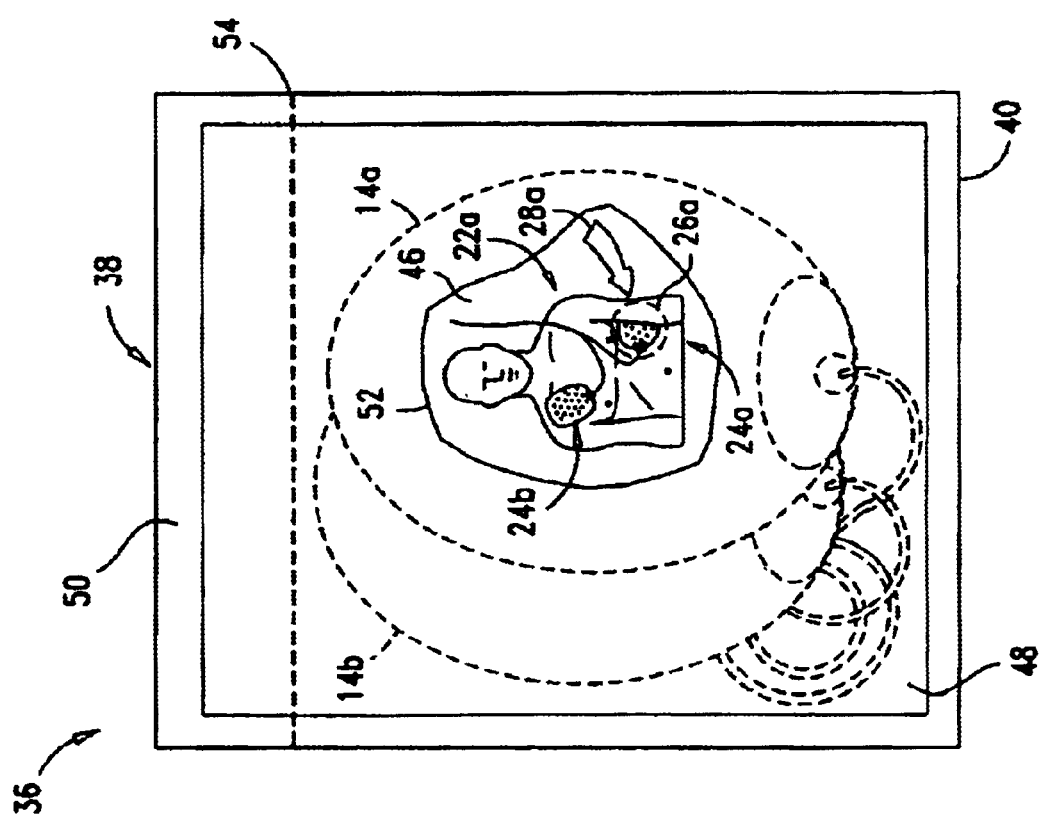
FIG. 3A is front view of a partially see-through defibrillator-electrode-pad storage system according to an embodiment of the invention.

FIGS. 3A and 3B are front and rear views, respectively, of a defibrillator-electrode-pad storage system 36, which includes a pair of defibrillator electrode pads 14a and 14b and a package 38 having a front side 40, an opaque rear side 42 having instructions 44, and a translucent window 46 disposed in the front side 40 according to an embodiment of the invention. Here, "translucent" means that the window 46 need not be perfectly clear—although it can be—but only clear enough for one to see through. Furthermore, although the defibrillator-electrode-pad storage system 36 is discussed as including a pair of defibrillator electrode pads 14a and 14b, the system 36 may include more or fewer electrode pads 14. In addition, although the system 36 is discussed as part of an AED system (FIG. 5), the system 36 or a similar electrode-pad storage system can be used with other medical devices or systems such as a heart monitor (not shown).

The translucent window 46 allows an AED operator (not shown in FIG. 3A) to view the defibrillator electrode pad 14a, instructions, or a label such as the picture 22a before he/she opens the package 38. Thus, the operator can often attach the electrode pads 14a and 14b to a patient (not shown) more quickly because he/she can determine which electrode pad goes where before he/she opens the package 38. The operator is also less likely to open the package 38, and thus waste the electrode pads 14a and 14b, if the electrode pads are inappropriate for the patient because he/she can determine the type of the electrode pads before he/she opens the package.

In addition to allowing the operator to view the defibrillator electrode pad 14a, the package 38 provides a moisture barrier that maintains the viability of the electrode pads 14a and 14b for a predetermined period and that otherwise protects the electrode pads. The front and rear sides 40 and 42 of the package 38 are formed from a material or materials that provide a suitable moisture barrier. For example, an opaque portion 48 of the front side 40 and the opaque rear side 42 may be formed from a polypropylene- or polyethylene-coated metal film. The translucent window 46 may be formed from Topas®, which is produced by Ticona, Aclar®, which is produced by Honeywell, or partially metallic clear film like the anti-static film used to package static-sensitive semiconductor components. The front and rear sides 40 and 42 are sealed together along the edges 50 of the package 38, and the window 46 and the opaque portion 48 are sealed together along or beyond the edge 52 of the window 46. For example, the front 40 may be conventionally sealed to the rear 42 and the window 46 conventionally sealed to the opaque portion 48 with heat or with a moisture-barrier adhesive. A tear line 54 may be disposed in the front side 40, the rear side 42, or both the front and rear sides to facilitate opening of the package 38. The tear line 54, however, typically does not degrade the moisture-barrier capabilities of the package 38.

Still referring to FIGS. 3A and 3B, during an emergency where it is determined that a patient (not shown) may need a shock, the operator (not shown in FIGS. 3A and 3B) retrieves the defibrillator-electrode-pad storage system 36, looks through the window 46 to determine the electrode-pad type or the appropriate attachment location of the electrode pad 14a, and opens the package 38 if the electrode pads 14a and 14b are of the type appropriate for the patient. Because the operator can determine the appropriate attachment location of the electrode pad 14a before or while opening the package 38, he/she can attach the electrode pads 14a and 14b to the patient without pausing to study the picture 22a after opening the package.

Figure 3C:
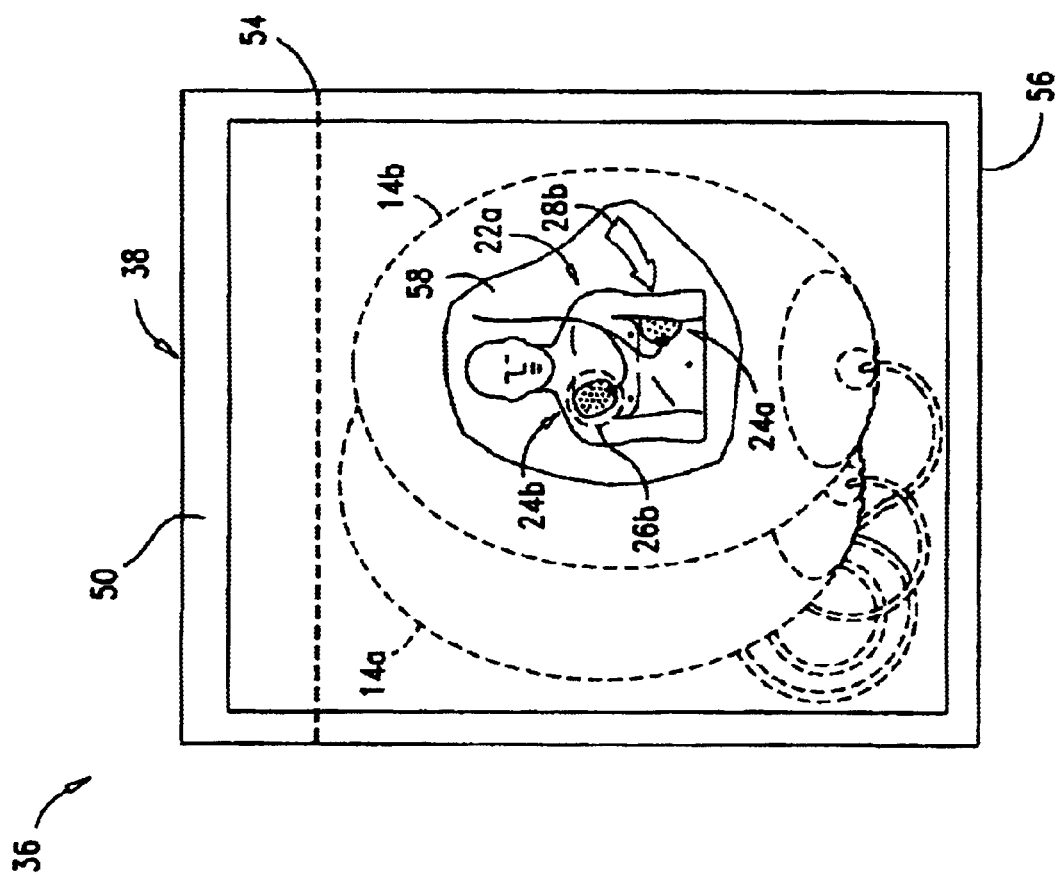
FIG. 3C is a rear view of the defibrillator-electrode-pad storage system of FIG. 3A according to another embodiment of the invention.

FIG. 3C is a rear view of the defibrillator-electrode-pad system 36 having a rear side 56 with a translucent window 58 according to another embodiment of the invention. The partially see-through rear side 56 replaces the opaque rear side 42 of FIG. 3B and is similar to the front side 40 of FIG. 3A. The window 58, which is similar to the window 46 of FIG. 3A, allows the operator (not shown FIG. 3C) to view the electrode pad 14b, instructions, or a label such as the picture 22b before he/she opens the package 38. Therefore, the operator can determine the electrode-pad type or the appropriate placement locations before opening the package 38 regardless of which side of the package he/she views.

Referring to FIGS. 3A–3C, other embodiments of the defibrillator-electrode-pad storage system 36 are contemplated. For example, although described as having front and rear sides, the package 38 can have a unibody construction with no distinct sides. Furthermore, although the windows 46 and 58 are shown as round, they may have other shapes. In addition, although the electrode-pad leads (e.g., leads 18 of FIG. 5) are shown as being stored inside the package 38, they may extend from through the package via a sealed lead opening. Moreover, although the pictures 22a and 22b are shown to be visible through the respective windows 46 and 58, other types of instructions or labels, such as a color to indicate the electrode-pad type, may be visible. Furthermore, although the instructions 44 are shown on the rear side 42, they may be on the window 46 or the opaque portion 48 of the front side 42, or on the window 58 or the opaque portion of the rear side 56.

Figure 4B:
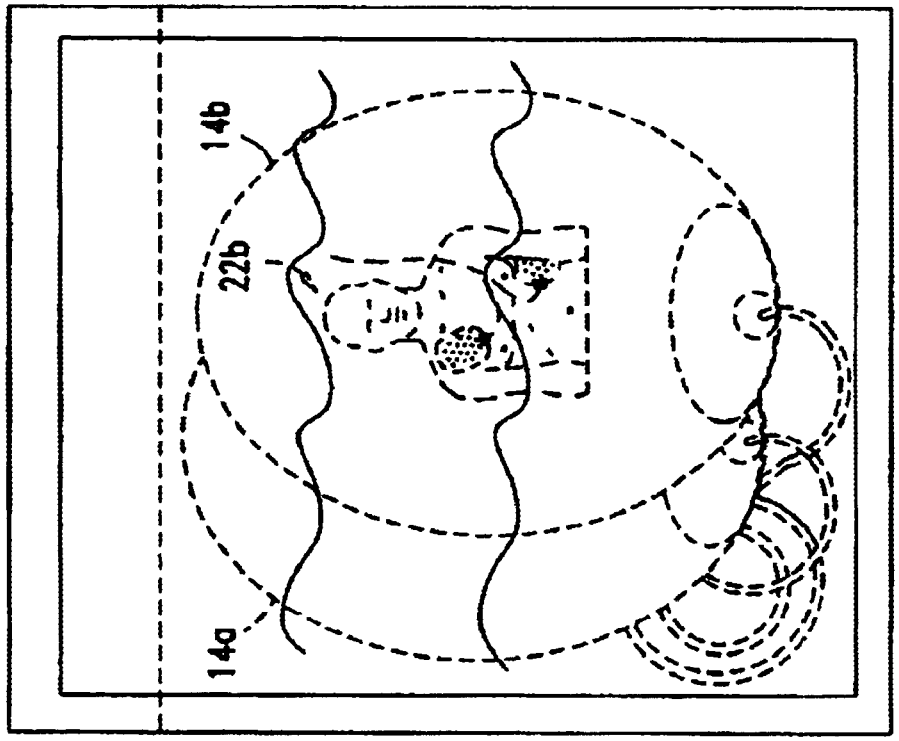
FIG. 4B is a rear view of the defibrillator-electrode-pad storage system of FIG. 4A according to an embodiment of the invention.
Figure 4A:
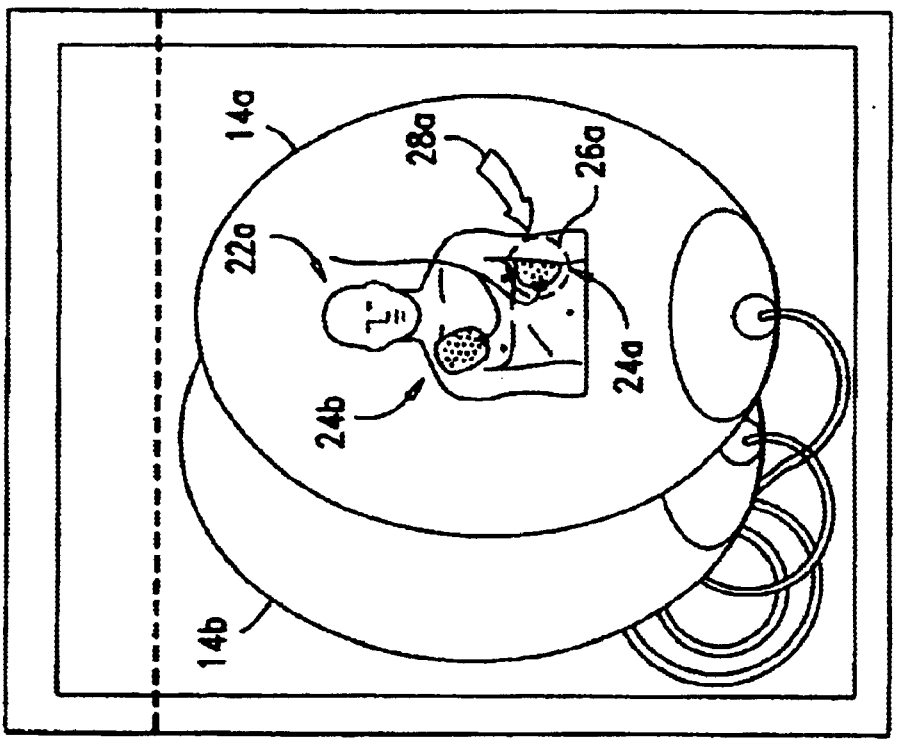
FIG. 4A is a front view of a fully see-through defibrillator-electrode-pad storage system according to an embodiment of the invention.

FIGS. 4A and 4B are front and rear views, respectively, of a defibrillator-electrode-pad storage system 60, which includes the defibrillator electrode pads 14a and 14b and a package 62 having a translucent front side 64 and an opaque rear side 66 according to an embodiment of the invention. The package 62 is similar to the package 38 of FIGS. 3A and 3B except that the entire front side 64 is translucent, and thus has no opaque portion.

Figure 4C:
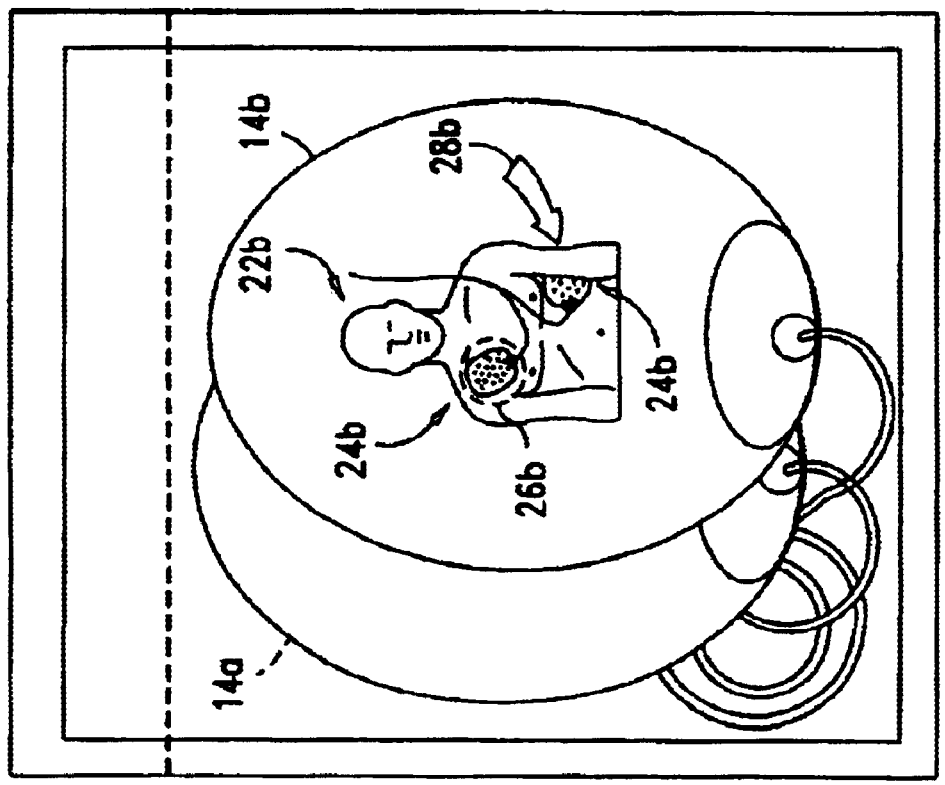
FIG. 4C is a rear view of the defibrillator-electrode-pad storage system of FIG. 4A according to another embodiment of the invention.

FIG. 4C is a rear view of the defibrillator-electrode-pad storage system 60 having a translucent rear side 68 according to another embodiment of the invention. The rear side 68 replaces the opaque rear side 66 of FIG. 4B and is similar to the front side 64 of FIG. 4A. The rear side 68 is also similar to the rear side 56 of FIG. 3C except that the entire rear side 68 is translucent, and thus has no opaque portion.

Figure 5:
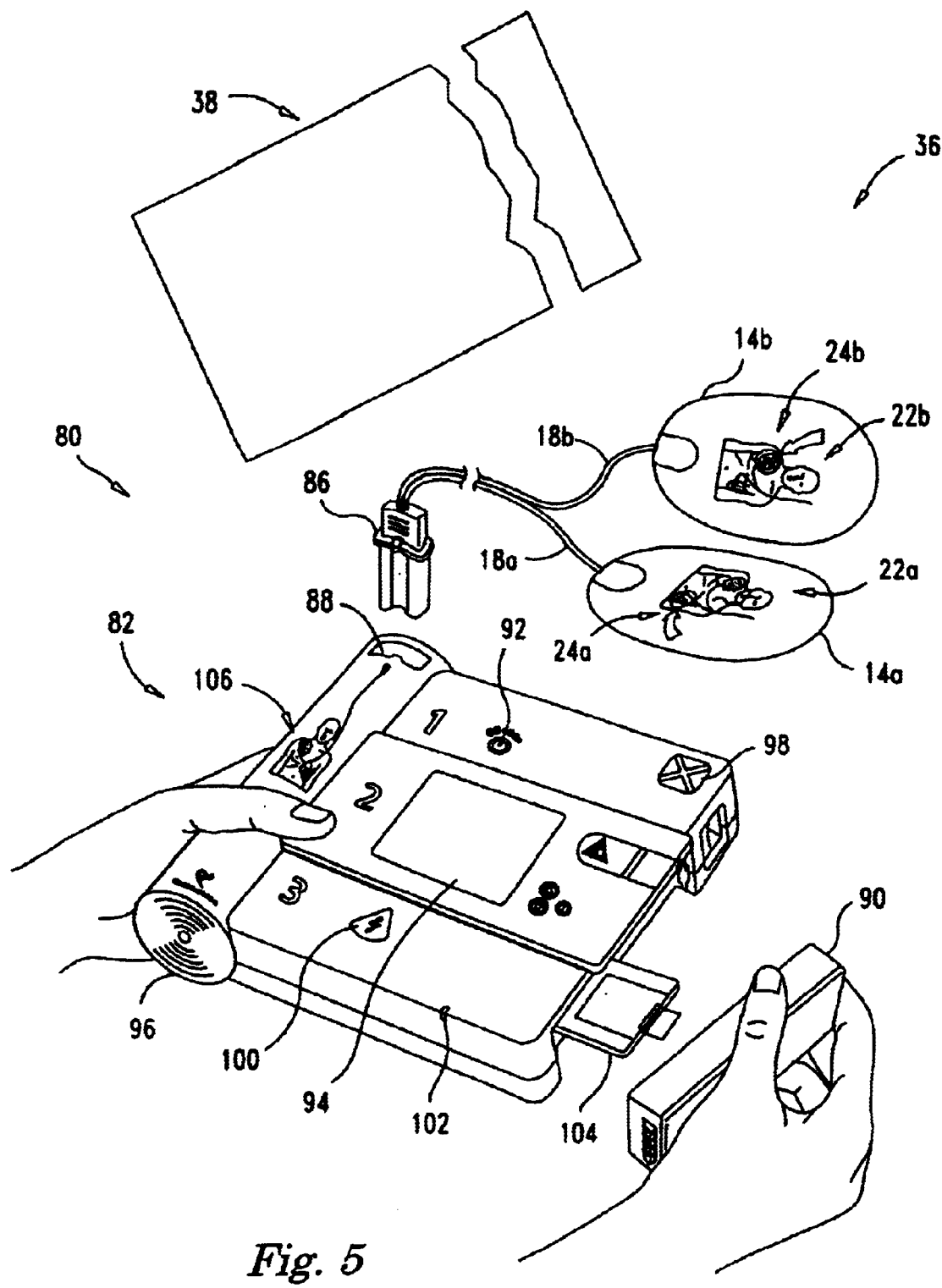
FIG. 5 is a perspective view of an AED system that incorporates the defibrillator-electrode-pad storage system of FIGS. 3A–3C or the system of FIGS. 4A–4C according to an embodiment of the invention.

FIG. 5 is a perspective view of an AED system 80, which includes an AED 82 for generating a shock and which includes the defibrillator-electrode-pad storage system 36 of FIGS. 3A–3C or the system 60 of FIGS. 4A–4C according to an embodiment of the invention. For clarity, the system 80 is discussed as including the electrode-pad storage system 36 of FIGS. 3A–3C, and the electrode pads 14a and 14b are shown removed from the opened package 38. In one embodiment, the storage system 36 includes a connector 86, which couples the electrode pads 14a and 14b to a connector 88 of the AED 82. Because they are not affected by moisture loss, the connector 86 and the electrode-pad leads 18a and 18b need not be—but can be—sealed within the package 38. If the connector 86 and the leads 18a and 18b extend from the package 38 via a sealed lead opening, then the operator (hand shown) can couple the connector 86 to the connector 88 before opening the package 38.

The AED 82 includes a battery 90 for supplying power, a main on/off key switch 92, a display 94 for displaying operator instructions, cardiac waveforms, or other information, a speaker 96 for providing audible operator instructions, an AED status indicator 98, and a shock button 100, which the operator presses to deliver a shock to the patient. The AED 82 may also include a microphone 102 for recording the operator's voice and other audible sounds that occur during the rescue, and a data card 104 for storing these sounds along with the patient's ECG and a record of AED events for later study.

Still referring to FIG. 5, during an emergency where it is determined that a patient (not shown) may need a shock, the operator retrieves the AED 82 and installs the battery 90 if it is not already installed. Next, the operator removes the defibrillator electrode pads 14a and 14b from the package 38 and inserts the electrode-pad connector 86 into the connector 88. Then, the operator turns the on/off switch 92 to the "on" position to activate the AED 82. Following the instructions displayed on the display 94 or "spoken" via the speaker 96, the operator attaches the electrode pads 14a and 14b to the patient at the respective locations 24a and 24b as shown in the pictures 22a and 22b and in a picture 106 on the AED 82. After the operator attaches the electrode pads 14a and 14b to the patient, the AED 82 analyzes the patient's ECG to determine whether the patient is suffering from a shockable heart rhythm. If the AED 82 determines that the patient is suffering from a shockable heart rhythm, then the display 94 or the speaker 96 instructs the operator to depress the shock button 100 to deliver a shock to the patient. Conversely, if the AED 82 determines that the patient is not suffering from a shockable heart rhythm, the display 94 or the speaker 96 informs the operator not to shock the patient, and may inform the operator to seek appropriate non-shock treatment for the patient. Furthermore, when it informs the operator not to shock the patient, the AED 82 often disables the shock button 100.

Figure 6:
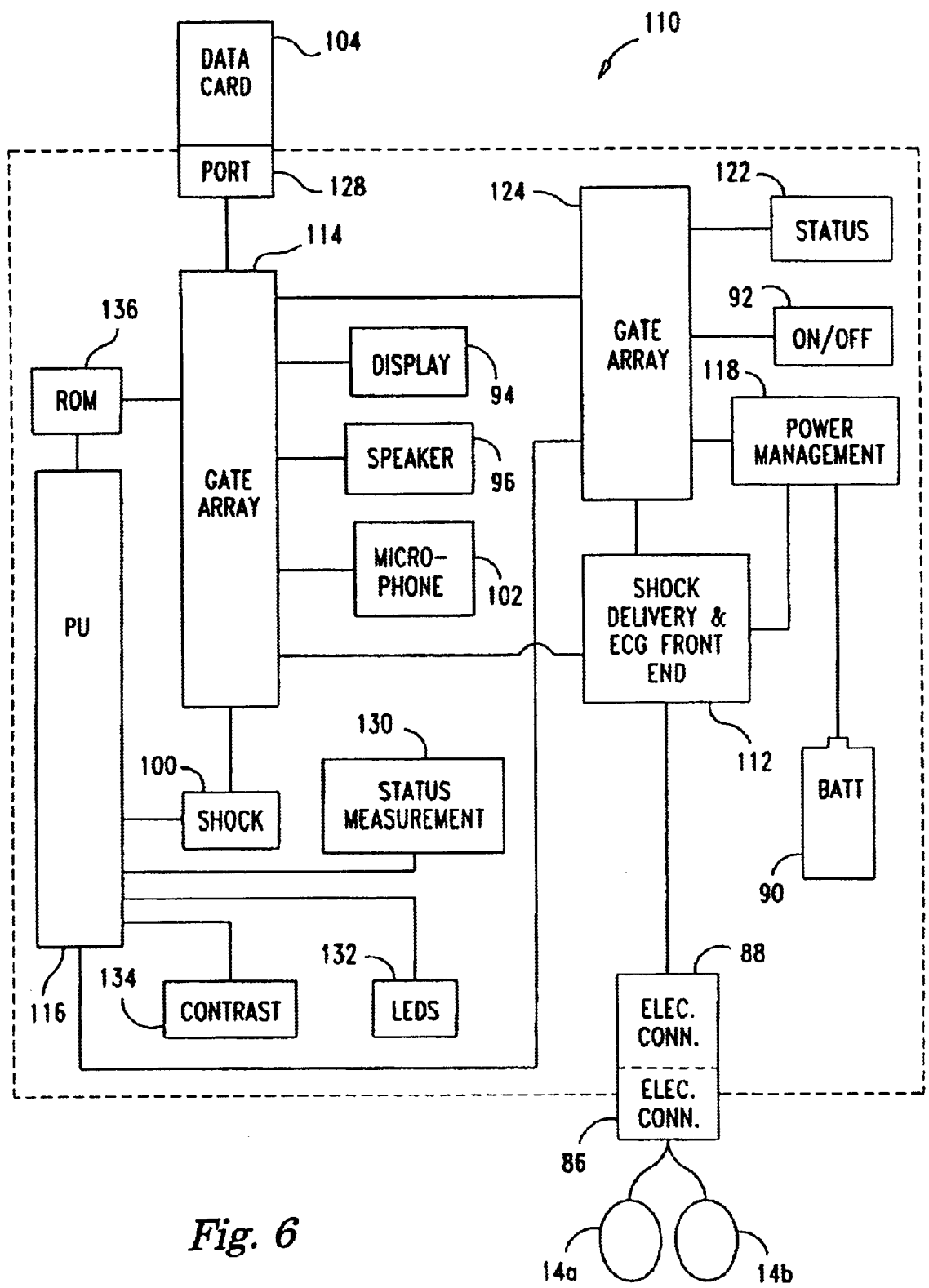
FIG. 6 is a block diagram of an AED circuit that the AED of FIG. 5 incorporates according to an embodiment of the invention.

FIG. 6 is a block diagram of an AED circuit 110, which the AED 82 of FIG. 5 can incorporate according to an embodiment of the invention. The defibrillator electrode pads 14a and 14b are coupled to the circuit 110 via the connectors 86 and 88 and are operable to sense a patient's ECG (not shown) and to apply an electrical shock to the patient (not shown). A shock-delivery-and-ECG front-end circuit 112 samples the patient's ECG during an analysis mode of operation and provides a shock to the patient via the connectors 86 and 88 and the electrode pads 14a and 14b during a shock-delivery mode of operation. A gate array 114 receives the ECG samples from the circuit 112 and provides them to a processor unit (PU) 116, which stores and analyzes the samples. If analysis of the patient's ECG indicates that the patient is suffering from a shockable heart rhythm, then the processor unit 116 instructs the circuit 112 via the gate array 114 to enable delivery of a shock when an operator (not shown in FIG. 6) presses the shock button 100. Conversely, if analysis of the patient's ECG indicates that the patient is not suffering from a shockable heart rhythm, then the processor unit 116 often disables the circuit 112 from delivering a shock to the patient.

Still referring to FIG. 6, the circuit 110 includes a power-management circuit 118 for distributing power from the battery 90 to the subcircuits of the circuit 110. The on/off switch 92 turns the circuit 110 "on" and "off", a status circuit 122 indicates the status of the circuit 110, and a gate array 124 interfaces the power-management circuit 118, the on/off circuit 92, and the status circuit 122 to the circuit 112, the processor unit 116, and the gate array 114. As discussed above in conjunction with FIG. 5, the display 94 displays information to an operator, the speaker 96 provides audio instructions to the operator, and the microphone 102 records the operator's voice and other audible sounds. The data card 104 is connected to the gate array 114 via a port 128. The card 104 stores the operator's voice and other sounds along with the patient's ECG and a record of AED events for later study. A status-measurement circuit 130 provides the status of the circuit 110 subcircuits to the processor unit 116, and LEDs 132 provide information to the operator such as whether the processor unit 116 has enabled the circuit 112 to deliver a shock to the patient. A contrast button 134 allows the operator to control the contrast of the display screen 94, and a memory such as a read only memory (ROM) 136 stores programming information for the processor unit 116 and the gate arrays 114 and 124.

The AED circuit 110 and other AED circuits are further discussed in the following references, which are incorporated by reference: U.S. Pat. Nos. 5,836,993, 5,735,879 entitled ELECTROTHERAPY METHOD AND APPARATUS, U.S. Pat. No. 5,607,454 entitled ELECTROTHERAPY METHOD AND APPARATUS, and U.S. Pat. No. 5,879,374 entitled DEFIBRILLATOR WITH SELF-TEST FEATURES.

What is claimed:

1. An electrode-pad package, comprising:
    a first side having a see-through portion;
    a second side, wherein said first side and said second side are directly sealed to one another along edges of the package; and
    a package interior disposed between the first and second sides and operable to store an electrode pad,
        wherein the first side has an opaque portion adjacent to the see-through portion, and
        further wherein the second side is opaque, and
        still further wherein the seal and the first and second sides inhibit moisture loss from the package interior.

2. The electrode-pad package of claim 1 wherein the second side has a see-through portion.

3. The electrode-pad package of claim 1 further comprising electrode pad instructions disposed on the first side of the package.

4. The electrode-pad package of claim 1 further comprising electrode pad instructions disposed on the second side of the package.

5. The electrode-pad package of claim 1 wherein the first and second sides inhibit moisture loss from the package interior.

6. The electrode-pad package of claim 1 further comprising a pad-lead opening.

7. The electrode-pad package of claim 1 wherein the first and second sides are flexible.

8. An electrode-pad storage system, comprising:
    an electrode-pad package comprising:
    a first side,
    a second side, wherein the second side is opaque and wherein said first side and said second side are directly sealed to one another along edges of the package,
    a translucent window disposed in the first side;
    a package interior disposed between the first and second sides;
    a first electrode pad disposed within the package interior; and
    instructions disposed on the first electrode pad,
        wherein the instructions are visible through the first translucent window.

9. The electrode-pad storage system of claim 8, further comprising:
    wherein the first electrode pad includes a backing;
    instructions disposed on the backing of the first electrode pad; and
    wherein the first electrode pad is positioned within the package interior such that the instructions are visible through the first translucent window.

10. The electrode-pad storage system of claim 8, further comprising:
    a second electrode pad disposed within the package interior;
    a second translucent window disposed in the second side;
    a first set of instructions disposed on the first electrode pad;
    a second set of instructions disposed on the second electrode pad; and
    wherein the first and second sets of instructions are respectively visible through the first and second translucent windows.

11. The electrode-pad storage system of claim 8, further comprising:
    wherein the first electrode pad has a conductive-layer side and a front side;
    a second layer pad disposed within the package interior and having a conductive-layer side and a front side;
    a second translucent window disposed in the second side of the package;
    a first set of instructions disposed on the front side of the first electrode pad;
    a second set of instructions disposed on front side of the second electrode pad; and
    wherein the conductive-layer side of the first electrode pad faces the conductive-layer side of the second electrode pad such that the first and second sets of instructions are respectively visible through the first and second translucent windows.

12. The electrode-pad storage system of claim 8, further comprising:
    wherein the first electrode pad has a conductive layer;
    a contact gel disposed on the conductive layer and having a moisture content;
    wherein the first and second sides are operable to maintain the viability of the contact gel for a predetermined time by inhibiting moisture loss from the package interior.

13. The electrode-pad storage system of claim 8, further comprising:
    wherein the first electrode pad has a conductive layer;
    a contact gel disposed on the conductive layer and having a moisture content;
    wherein the first and second sides are operable to maintain the moisture content of the contact gel above a predetermined level for a predetermined time.

14. The electrode-pad storage system of claim 8, further comprising:
    wherein the first electrode pad has a conductive layer;
    a contact gel disposed on the conductive layer;
    a seal disposed where the first side is attached to the second side; and
    wherein the first and second sides and the seal are operable to maintain the viability of the contact gel for a predetermined time by inhibiting moisture loss from the package interior.

15. The electrode-pad storage system of claim 8, further comprising:
    wherein the first electrode pad has a conductive layer;
    a contact gel disposed on the conductive layer and having a moisture content;
    a seal disposed where the first side is attached to the second side; and
    wherein the first and second sides and the seal are operable to maintain the moisture content of the contact gel at or above a predetermined level for a predetermined time.

16. The electrode-pad storage system of claim 8, further comprising: an electrode pad lead coupled to the first electrode pad and disposed within the package interior.

17. The electrode-pad storage system of claim 8, further comprising:
wherein the electrode-pad package comprises a sealed lead opening; and
an electrode-pad lead that coupled to the first electrode pad and extending from the package interior through the sealed lead opening.

18. The electrode-pad storage system of claim 8 wherein the first electrode pad comprises a first defibrillator electrode pad.

19. The electrode-pad storage system of claim 8 wherein the first electrode pad comprises a first monitor electrode pad.

20. An defibrillator system, comprising:
a defibrillator; and
a defibrillator-electrode pad storage system, comprising,
a defibrillator-electrode pad package comprising,
a first side,
a second side, wherein said first side and said second side are directly sealed to one another along edges of the package,
a translucent window disposed in the first side, and
a package interior disposed between the first and second sides, and
a defibrillator electrode pad disposed within the package interior,
wherein the first side has an opaque portion adjacent to the translucent window, and
further wherein the second side is opaque, and
still further wherein the seal and the first and second sides inhibit moisture loss from the package interior.

21. The defibrillator system of claim 20 wherein the defibrillator automatic or semi-automatic external defibrillator.

22. The defibrillator system of claim 20 wherein the defibrillator-electrode-pad storage system is attachable to the defibrillator.

23. The defibrillator system of claim 20 further comprising:
wherein the defibrillator comprises a first connector;
wherein the defibrillator-electrode-pad package comprises a sealed lead opening;
an electrode-pad lead that extends from the package interior through the sealed lead opening the electrode-pad lead having a first end coupled to the defibrillator electrode pad and having a second end that is disposed outside of the package interior; and
a second connector coupled to the second end of the electrode-pad lead and attachable to the first connector.

24. A method, comprising:
viewing an electrode pad through a window disposed in a side of an electrode-pad package, wherein said package has a first side and a second side that are directly sealed to one another along edges of the package; and
removing the electrode pad from the package after viewing the electrode pad,
wherein the first side has an opaque portion adjacent to the translucent window, and
further wherein the second side is opaque, and
still further wherein the seal and the first and second sides inhibit moisture loss from the package interior.

25. The method of claim 24 further comprising attaching the electrode pad to a patient after removing the electrode pad from the package.

26. The method of claim 24 further comprising attaching the electrode pad to a medical device after removing the electrode pad from the package.

27. The method of claim 24 further comprising:
wherein the electrode pad comprises a defibrillator electrode pad; and
attaching the defibrillator electrode pad to a defibrillator after removing the defibrillator electrode pad from the package.

28. A method, comprising:
viewing an instruction through a window disposed in a side of a package, wherein said package has a first side and a second side that are directly sealed to one another along edges of the package, the instruction disposed on an electrode pad that is located inside of the package; and
removing the electrode pad from the package after viewing the instruction,
wherein the first side has an opaque portion adjacent to the window, and
further wherein the second side is opaque, and
still further wherein the seal and the first and second sides inhibit moisture loss from the package interior.

29. The method of claim 28 wherein the instruction comprises an illustration.

30. A method, comprising:
viewing a first electrode pad through a window disposed in a side of a first electrode-pad package, wherein said package has a first side and a second side that are directly sealed to one another along edges of the package;
determining that the first electrode pad is inappropriate for a patient;
viewing a second electrode pad through a window disposed in a side of a second electrode-pad package, wherein said package has a first side and a second side that are directly sealed to one another along edges of the package;
determining that the second electrode pad is appropriate for the patient; and
removing the electrode pad from the second package after determining that the second electrode pad is appropriate for the patient,
wherein the first side of the first electrode pad package and the first side of the second electrode pad package each has an opaque portion adjacent to the see-through portion, and
further wherein the second side of the first electrode pad package and the second side of the second electrode pad package is opaque, and
still further wherein the seal and the first and second sides of the first electrode pad package and the second electrode pad package inhibit moisture loss from the package interior.

31. The method of claim 30, further comprising attaching the second electrode pad to the patient after removing the second electrode pad from the second package.

32. The method of claim 30, further comprising attaching the second electrode pad to a medical device after removing the second electrode pad from the second package.

* * * * *